US00PP08600P

United States Patent [19]

Resendez

[11] Patent Number: Plant 8,600

[45] Date of Patent: Feb. 15, 1994

[54] *LAGERSTROEMIA INDICA* CV. MONED

[75] Inventor: Gilbert N. Resendez, La Verne, Calif.

[73] Assignee: Monrovia Nursery Company, Azusa, Calif.

[21] Appl. No.: 449

[22] Filed: Jan. 4, 1993

[51] Int. Cl.[5] ..... A01H 5/00
[52] U.S. Cl. ..... Plt./67.3
[58] Field of Search ..... Plt. 67.3

*Primary Examiner*—James R. Feyrer

[57] ABSTRACT

A new and distinct selection of Crape Myrtle shrub which shall be referred to hereinafter as *Lagerstroemia indica* cultivar Moned. *Lagerstroemia indica* cultivar Moned differs distinctively from other *Lagerstroemia indica* plants by its unique combination of a floriferous habit of rosy-red, thick textured flowers and a dwarf size and a more dense compact growth habit.

1 Drawing Sheet

BACKGROUND OF THE NEW PLANT

This invention relates to a new and distinct selection of *Lagerstroemia indica*, a member of the lythraceae or Loosestrife family. *Lagerstroemia indica* cultivar Moned was discovered in a group of seedlings which originated from seed of *Lagerstroemia indica* 'Little Chief', seed was sown November 1983. During the summer of 1987, this new cultivar was selected at Monrovia Nursery Company, 18331 East Foothill Boulevard, Azusa, Calif. My new plant has been asexually reproduced by cuttings since 1987 at the above location in Azusa at Monrovia Nursery Company. The original seedlings displayed extreme variability, therefore the distinct phenotypic characteristics of my new selection that sets this plant apart from other *Lagerstroemia indica* plants would likely be lost through sexual reproduction. Therefore, sexual reproduction is prohibited and propagation is restriced to asexual reproduction by cuttings.

SUMMARY OF INVENTION

*Lagerstroemia indica* cv. Moned is unusual and unique in the dwarf growth habit. Normal *Lagerstroemia indica* is generally a tree achieving heights of 30 feet. The group of 'Petite' named *Lagerstroemia indica* will achieve heights of 15 feet. To date the largest *Lagerstroemia indica* 'Moned' is 3 feet tall by 4 feet wide. My new selection should achieve a height of 6 feet and a spread of 6 feet.

*Lagerstroemia indica* cv. Moned is extremely floriferous. In the southern California region, blossoms appear from late May through Mid-November on plants which have been lightly trimmed to remove spent flowers.

Other *Lagerstroemia indica* selections that grow in the southern California are a normally bloom from mid-July to mid-September.

Cold tolerance has not been tested in regions colder than 0° F.—the cold tolerant range for *Lagerstroemia indica* to which this cultivar is derived.

Therefore, it is assumed 0° is the lowest cold hardiness rating.

Tolerance or susecptibility to powdery midew and aphids have not been cited as a problem in Azusa growing grounds, in other conditions this has not been tested.

BRIEF DESCRIPTION OF DRAWINGS

The upper photograph exhibits a close-up of the flowers and demonstrates how the floriferous habit practically covers the plant when in bloom.

The lower photograph displays the overall dense compact growth habit.

BOTANICAL DESCRIPTION

Below is a detailed description of my new selection of *Lagerstroemia indica* cv. Moned, the color terminology is from The British Horticultural Colour Charts.

Overall size and habit: Dwarf shrub, this plant does not have a dominant leader. Natural branching occurs at the base near soil line. Secondary branches occur close together with a spacing of 1.5 cm to 2.5 cm range between branches. The internode length between leaves on the secondary branches range from 0.5 cm to 1 cm in length. After 5 years, the plant is expected to achieve a height of about 6 feet and a spread of 6 feet.

Branching: Strength and sturdiness appears storng upholding branches with terminal panicles in full bloom.

Flowering habit: A 2½ year old plant in July exhibits over 90% of the terminals with flower panicles. Ninety-three panicles were counted on my selection which in overall size was 50–56 cm in width and 23 cm in height.

Flower: In southern California, ruffled flowers appear from late May through mid-November.

*Arrangement.*—Terminal panicles.

*Color.*—Tyrian Purple 727, no fading with age. Flower color appears identical to the cultivar Cherokee.

*Sahpe.*—Petals — the limb crinkly, the claw long and slender, Calyx-smooth and glabrous, lobes generally six.

*Size.*—Diameter—Ranging 3.0 cm to 4.0 cm, natural — not pressed. Diameter widening as petals become more horizontal with age Length of petal — Claw 0.5 to 0.75 cm. Limb 1 cm. Width of petal — Limb 13–1.5 cm, natural — not pressed Leaf:

*Arrangement.*—Opposite — Alternate on young growth, short-petioled.

*Size.*—Length varies 2.7 cm–4 cm. Width varies 2 cm–2.5 cm.

*Color.*—Above — Parsley green 00962, surface puberulent. Underside — Spinach green 0960/2.

*Shape.*—Elliptic.

*Margins.*—Entire.

*Autumn color.*—Normal, not unusually colorful.

*Senescence.*—completed by mid-December in southern California.

Bark: Color and texture are generally an identifying characteristic on Lagerstroemia, however, due to the dense shrubby habit, the bark is not visible.

Fruit: A woody capsule, not observed as these plants have all been lightly sheared removing fruit that may develop. Fertility unknown.

*Style and pistil.*—one.

*Stamen.*—approximately 30, arranged within the tube.

*Anthers.*—yellow color.

*Filaments.*—pink color.

I claim:

1. A new and distinct variety of *Lagerstroemia* plant as substantially shown and described herein, that is characterized particularly as a novelty by the unique combination of a floriferous habit of rosy-red, thick textured flowers and a dwarf overall size and more dense compact growth habit.

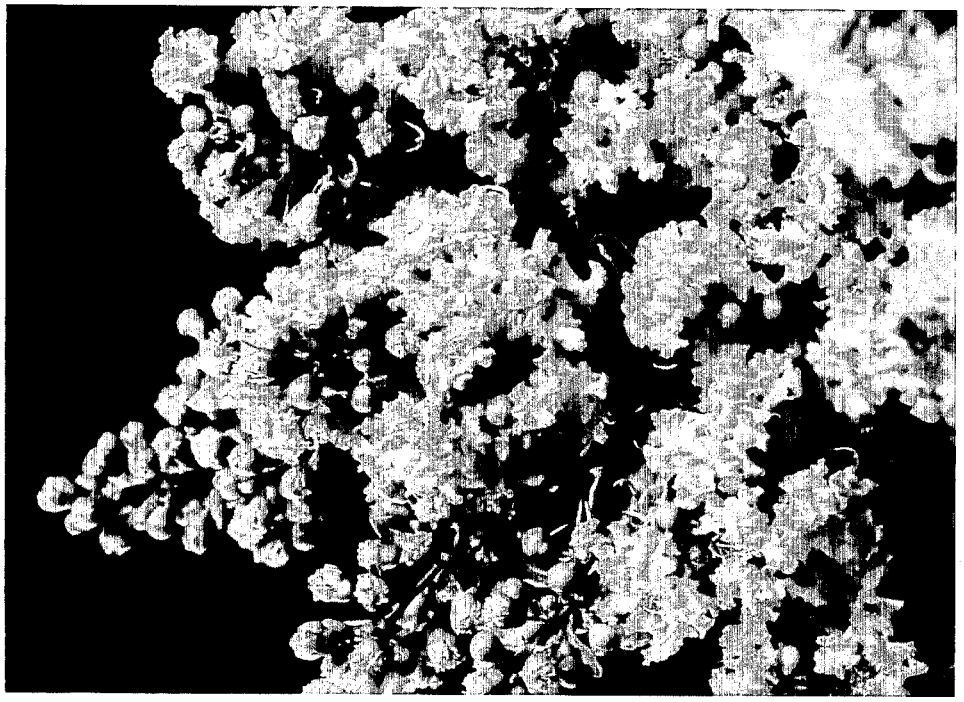
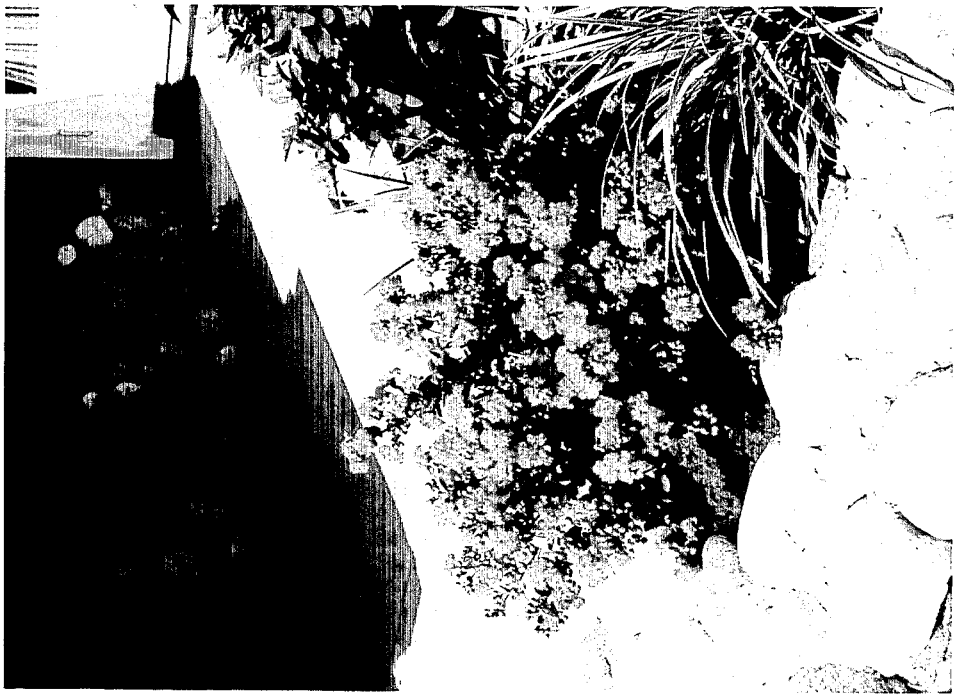

* * * * *